United States Patent [19]
Young et al.

[11] Patent Number: 6,107,316
[45] Date of Patent: Aug. 22, 2000

[54] METHOD FOR TREATING PROTOZOAL INFECTIONS

[75] Inventors: David Hamilton Young, Ambler; Enrique Luis Michelotti, Fort Washington; Thomas David Edlind, Wyndmoor; Santosh Kumar Katiyar, Philadelphia, all of Pa.

[73] Assignee: Rohm and Haas Company, Philadelphia, Pa.

[21] Appl. No.: 09/069,402

[22] Filed: Apr. 29, 1998

Related U.S. Application Data

[60] Provisional application No. 60/045,267, May 1, 1997.

[51] Int. Cl.$^7$ .......................... A01N 43/72; A01N 43/36; C07D 403/12; C07D 273/01
[52] U.S. Cl. ........................ 514/359; 514/365; 514/374; 514/372; 514/378; 514/383; 514/439; 514/461; 514/514; 546/146; 546/156; 548/200; 548/214; 548/236; 548/248; 548/255; 548/262; 548/399
[58] Field of Search ..................... 514/359, 365, 514/374, 378, 372, 461, 514; 548/248, 236, 214, 200, 255, 262, 399

[56] References Cited

U.S. PATENT DOCUMENTS

| | | | |
|---|---|---|---|
| 3,661,991 | 5/1972 | McNulty et al. | 564/186 |
| 4,822,902 | 4/1989 | Carley et al. | 558/14 |
| 4,863,940 | 9/1989 | Sharma | 514/359 |
| 5,254,584 | 10/1993 | Michelotti et al. | 514/514 |
| 5,304,572 | 4/1994 | Michelotti et al. | 514/514 |

*Primary Examiner*—James O. Wilson
*Assistant Examiner*—Howard Owens
*Attorney, Agent, or Firm*—Thomas D. Rogerson

[57] ABSTRACT

A method for treating protozoal infections is described. The method employs N-acetonylbenzamide compounds provided in an effective amount to inhibit the growth of protozoans. The compounds are useful in controlling such protozoan parasites as *Giardia lamblia, Leishmania major, Entamoeba histolytica, Cryptosporidium parvum, Toxoplasma gondii* and microsporidia.

7 Claims, No Drawings

METHOD FOR TREATING PROTOZOAL INFECTIONS

This is a Continuation of application Ser. No. 60/045,267, filed May 1, 1997, now abandoned.

The present invention relates to a method for the treatment or prophylaxis of protozoal infections in man or animals. In particular, the present invention relates to a method for treating protozoal infections by the use of certain N-acetonylarylamide derivatives known to inhibit the growth of fungi, see, for example, U.S. Pat. Nos. 3,661,991; 4,822,902; 4,863,940; 5,254,584 and 5,304,572.

Protozoa are unicellular eukaryotic microorganisms which lack cell walls, and usually are motile and colorless. They are distinguished from algae by their lack of chlorophyll, from fungi by their absence of a cell wall and the presence of motility, and from slime molds by their lack of fruiting body formation.

Protozoa are generally classified into four major groups based on their mechanisms of motility or life cycles. The flagellates are protozoa which employ from one to eight or so flagella for movement. The ciliates employ cilia, which are shorter than flagella and present in large numbers. Protozoa which move by extending pseudopodia are called amoeba. The fourth major group are the sporozoa or apicomplexa, which are non-motile, intracellular parasites (except during their sexual stage) and penetrate host cells by a mechanism involving their characteristic apical complex. Some protozoa do not fit into any of these four groups, such as the non-motile, intracellular microsporidia, which penetrate host cells by an injection mechanism.

Clinically important representatives of the flagellate group include *Giardia lamblia, Trichomonas vaginalis*, Leishmania spp., and Trypanosoma spp. *G. lamblia* is a waterborne intestinal parasite which occurs worldwide, causing diarrhea, and other intestinal symptoms. The most commonly used drugs used to treat giardiasis are metronidazole and other members of the 5-nitroimidazoles. Metronidazole is mutagenic in the Ames test {Vogd et al., Mutation Research, vol. 26, 483–490 (1974)} and has various toxic side effects. The development of resistance to these drugs in Giardia and other protozoan parasites such as *Entamoeba histolytica* and *Trichomonas vaginalis* also limits their effectiveness. Leishmaniasis, a life-threatening disease caused by Leishmania spp., is a major health problem worldwide with an estimated 10–15 million people infected and 400,000 new cases each year. There is currently no satisfactory treatment for leishmaniasis. The treatment of choice is pentavalent antimony in the form of sodium stibogluconate or meglumine antimonate. Both drugs are administered intravenously, have severe adverse side effects, require hospitalization during treatment and are not always effective {M. Ouelette and B. Papadopoulou, Parasitology Today, vol. 9, pp. 150–153 (1993)}. Trypanosoma spp. cause life-threatening diseases in humans, including African sleeping sickness and Chagas disease, as well as a number of important diseases in domestic animals. Leishmania and Trypanosoma are closely-related genera, representing the major pathogens in the kinetoplastid group of protozoa.

The ciliates are generally not pathogenic, except for *Balantidium coli* which is an intestinal parasite of domestic animals, in particular, swine. Occasionally, *B. coli* infects humans, producing a severe dysentery.

The amoeba group includes the intestinal parasite *Entamoeba histolytica* which causes amoebic dysentery and extraintestinal abscesses of organs such as the liver and lung. The most commonly used drug for treating *E. histolytica* infection is metronidazole. Other free-living amoeba which occassionally cause infections in humans include Acanthamoeba and Naegleria spp.; these infections are typically difficult to treat.

The Sporozoa comprise a large group of protozoa, all of which are obligate parasites. Representative sporozoans are Plasmodium spp. (causing malaria), *Toxoplasma gondii*, Cryptosporidium spp., Theileria spp. and Eimeria spp. (causing coccidiosis in fowl and domestic animals). *Toxoplasma gondii* is an important pathogen in immunocompromized patients and causes encephalitis, a dangerous life-threatening disease. The standard therapy for toxoplasmic encephalitis is a combination of pyrimethamine and sulfadiazine, however, side effects of this treatment are frequently so severe as to require discontinuation of the treatment. *Cryptosporidium parvum* is a common cause of intestinal infection leading to self-limited diarrhea, but in the immunocompromized individual *C. parvum* infection is chronic and life-threatening. There is currently no effective treatment for cryptosporidiosis.

Microsporidia are obligate, intracellular pathogens which cause intestinal and systemic infections in immunocompromised patients, as well as economically important infections in fish and invertebrates. Microsporidiosis in patients suffering from acquired immune deficiency syndrome (AIDS) is primarily associated with Encephalitozoon species (including *E. intestinalis, E. cuniculi*, and *E. hellem*) and *Enterocytozoon bieneusi*. Microsporidiosis is a frequent cause of chronic diarrhea in AIDS patients and may also be found outside of the intestine in the eye, biliary tract, nasal sinuses, urinary tract and respiratory tract.

Many currently used drugs for treatment of protozoal infections are not sufficiently effective, have harmful side effects and are difficult or expensive to administer. Consequently, there is an urgent need for new chemotherapeutic agents to combat protozoal parasites.

It has been surprisingly discovered that N-acetonylarylamide derivatives inhibit the growth of parasitic protozoans. A first aspect of the present invention is a method for treating protozoal infections comprising applying to the locus of a protozoan a compound having the formula I:

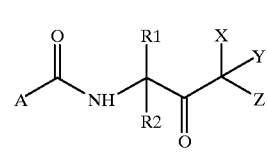

wherein:

A is selected from substituted and unsubstituted phenyl, pyridyl, furyl, thienyl, isoxazolyl, oxazolyl, pyrrolyl, isothiazolyl, thiazolyl, pyrazolyl, imidazolyl, pyrimidinyl, quinolyl, isoquinolyl, naphthyl, pyridazinyl, pyrazinyl, benzothienyl, indolyl, benzofuranyl, benzyl, ($C_3$–$C_7$)cycloalkyl, ($C_1$–$C_6$) alkyl, halo($C_1$–$C_6$)alkyl, ($C_2$–$C_6$)alkenyl, halo($C_2$–$C_6$) alkenyl, ($C_2$–$C_6$)alkynyl, and halo($C_2$–$C_6$)alkynyl wherein the substituents are independently selected from:
  a) one to four of halo, cyano, ($C_1$–$C_6$)alkyl, halo ($C_1$–$C_6$)alkyl, ($C_2$–$C_6$)alkenyl, halo($C_2$–$C_6$)alkenyl, ($C_2$–$C_6$)alkynyl, halo($C_2$–$C_6$)alkynyl, ($C_1$–$C_6$) alkoxy, halo($C_1$–$C_6$)alkoxy, ($C_1$–$C_6$)alkylthio, halo ($C_1$–$C_6$)alkylthio, nitro, —$NR^6R^7$, —$CR^8$=$NOR^9$, $NHCOOR^{10}$, —$CONR^{11}R^{12}$,—$COOR^{13}$;

b) fused five, six, and seven-membered rings formed from two such substituents; and c) a fused 5, 6 or 7 membered carbocyclic ring which may contain up to two heteroatoms selected from the group consisting of: O, S, N, and P:

$R^1$ and $R^2$ are each independently selected from H, $(C_1–C_6)$alkyl, halo$(C_1–C_6)$alkyl, $(C_2–C_6)$alkenyl, halo $(C_2–C_6)$alkenyl, $(C_2–C_6)$alkynyl, or halo$(C_2–C_6)$ alkynyl provided that at least one of $R^1$ and $R^2$ is other than H;

$R^6$ and $R^7$ are each independently selected from H, $(C_1–C_6)$alkyl, and $(C_1–C_6)$alkylcarbonyl;

$R^8$ is selected from H, $(C_1–C_6)$alkyl, $(C_2–C_6)$alkenyl, and $(C_2–C_6)$alkynyl;

$R^9$ is selected from H, $(C_1–C_6)$alkyl, $(C_2–C_6)$alkenyl, $(C_2–C_6)$alkynyl, and $(C_1–C_4)$alkylcarbonyl;

$R^{10}$, $R^{11}$, $R^{12}$ and $R^{13}$ are each independently selected from H, $(C_1–C_6)$alkyl, $(C_2–C_6)$alkenyl, and $(C_2–C_6)$alkynyl; and X, Y and Z are each independently selected from H, halo, cyano, thiocyano, isothiocyano and $(C_1–C_6)$ alkylsulfonyloxy, provided that at least one of X, Y and Z is halo, cyano, thiocyano, isothiocyano or $(C_1–C_6)$ alkylsulfonyloxy;

enantiomers and stereoisomers thereof; and physiologically acceptable acid addition salts thereof.

As used herein, the term "halo" means fluoro, bromo, chloro, or iodo.

The term "$(C_1–C_6)$alkyl" means a straight or branched saturated hydrocarbon group having from 1 to 6 carbons per group, and includes, e.g, methyl, ethyl, n-propyl, isopropyl, n-butyl, isobutyl, t-butyl, pentyl and hexyl. Halo-substituted alkyl groups, referred to as haloalkyl, include, for example, chloromethyl, trifluoromethyl, bromoethyl, pentafluoroethyl, iodopropyl, and chlorobutyl.

The term "$(C_2–C_6)$alkenyl" means a straight or branched group having at least one double bond and from 2 to 6 carbons per group, and includes, e.g, ethenyl, 2-propenyl, 2-butenyl and 2-methyl-2-propenyl.

The term "$(C_2–C_6)$alkynyl" means a straight or branched alkynyl group having at least one triple bond and from 2 to 6 carbons per group, and includes, e.g, ethynyl, 2-propynyl and 2-butynyl.

The term "$(C_1–C_6)$alkoxy" means a straight or branched alkoxy having from 1 to 6 carbons per group, and includes, e.g, methoxy, propoxy, n-butoxy and t-butoxy.

The term "$(C_1–C_6)$alkylthio" means a straight or branched alkylthio group having from 1 to 6 carbons per group, and includes, e.g., methylthio and propylthio.

"Haloalkyl", "haloalkenyl", "haloalkynyl", "haloalkoxy", and "haloalkylthio" groups are "alkyl," "alkenyl," "alkynyl," "alkoxy" and "alkylthio" groups, respectively, which have from 1 to 5 halogen substituents.

The term "$(C_3–C_7)$ cycloalkyl" includes, for example, cyclopropyl and cyclohexyl.

The term "$(C_1–C_6)$alkylcarbonyl" includes straight or branched alkyl groups having from 1 to 6 carbons per group which are connected to a carbonyl group, for example, methylcarbonyl and butylcarbonyl.

The term "$(C_1–C_6)$alkylsulfonyloxy" includes straight or branched alkyl groups having from 1 to 6 carbon atoms per group which are connected to a sulfonyloxy group, for example, methylsulfonyloxy and propylsulfonyloxy.

Suitable —$NR_6R_7$ moieties include amino, monosubstituted amino and disubstituted amino such as, for example, amino, methylamino, ethylamino, acetylamino, and diethylamino.

The term "nitro" means a group having the structural formula —$NO_2$.

The term "cyano" means a group having the structural formula —CN.

The term "thiocyano" means a group having the structural formula —SCN.

The term "isothiocyano" means a group having the structural formula —NCS.

Suitable —$CR^8$=$NOR^9$ moieties include, for example, hydroximinomethyl, methoxyiminomethyl, ethoxyiminomethyl, methoxyiminoethyl, and methylcarbonyloxyiminomethyl.

Suitable —$CONR^{11}R^{12}$ substituents include amido (—$CONH_2$), monosubstituted amido and disubstituted amido such as, for example, methylamido (—$CONHCH_3$), dimethylamido (—$CON(CH_3)_2$), propylamido, and dibutylamido.

Suitable $NHCOOR^{10}$ substituents include, for example, methylcarbamate and isopropylcarbamate.

Also contemplated for use in the method of the present invention are compounds having the structural formula (II) wherein $R^4$ and $R^5$ together form a fused 5, 6, or 7-membered ring, which may contain up to two heteroatoms selected from the group consisting of O, S, N, and P; $R^1$ and $R^2$ are H, $(C_1–C_6)$alkyl, halo$(C_1–C_6)$alkyl, $(C_2–C_6)$alkenyl, and $(C_2–C_6)$alkynyl, provided that at least one of $R^1$ and $R^2$ is not H; $R^3$ is selected from H, halo, cyano, $(C_1–C_6)$alkyl, halo$(C_1–C_6)$alkyl, $(C_2–C_6)$alkenyl, $(C_2–C_6)$alkynyl, $(C_1–C_6)$alkoxy, $(C_1–C_6)$alkylthio, halo$(C_1–C_6)$alkoxy, nitro, carboxyl, —$NR^6R^7$, —$CR^8$=$NOR^9$, $NHCOOR^{10}$, —$CONR^{11}R^{12}$, and —$COOR^{13}$, $R^6$, $R^7$, $R^8$, $R^9$, $R^{10}$, $R^{11}$, $R^{12}$, and $R^{13}$ are H or $(C_1–C_6)$ alkyl, and X and Y are each independently selected from H, halo, cyano, thiocyano, isothiocyano and $(C_1–C_6)$ alkylsulfonyloxy, provided that at least one of X and Y is not H.

Preferably, A is selected from substituted and unsubstituted phenyl, pyridyl, furyl, thienyl, isoxazolyl, oxazolyl, pyrrolyl, isothiazolyl, thiazolyl, pyrazolyl, imidazolyl, pyrimidinyl, quinolyl, isoquinolyl, naphthyl, pyridazinyl, pyrazinyl, benzothienyl, indolyl, benzofuranyl, benzyl, $(C_3–C_7)$cycloalkyl.

In a preferred embodiment of the method of the present invention, using compounds having the structural formula (I), A is phenyl and the compounds have the structural formula:

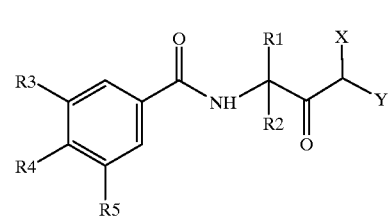

II wherein:

$R^1$ and $R^2$ are each independently selected from H, $(C_1–C_6)$ alkyl, halo$(C_1–C_6)$alkyl, $(C_2–C_6)$alkenyl, and $(C_2–C_6)$ alkynyl, provided that at least one of $R^1$ and $R^2$ is other than H;

$R^3$, $R^4$, and $R^5$ are each independently selected from the group consisting of H, halo, cyano, $(C_1–C_6)$alkyl, halo $(C_1–C_6)$alkyl, $(C_2–C_6)$alkenyl, $(C_2–C_6)$alkynyl, $(C_1–C_6)$ alkoxy, $(C_1–C_6)$alkylthio, halo$(C_1–C_6)$alkoxy, nitro, —$NR^6R^7$, —$CR^8$=$NOR^9$, $NHCOOR^{10}$, —$CONR^{11}R^{12}$, and —$COOR^{13}$;

$R^6$, $R^7$, $R^8$, $R^9$, $R^{10}$, $R^{11}$, $R^{12}$, and $R^{13}$ are each independently selected from H and $(C_1–C_6)$ alkyl; and X and Y are each independently selected from H, halo, cyano, thiocyano, isithiocyano and $(C_1-C_6)$ alkylsulfonyloxy, provided that at least one of X and Y is other than H.

In a particularly preferred embodiment of the method of the present invention, the compounds used have the structural formula (II), wherein X is chloro; Y is H; $R^1$ is methyl; $R^2$ is selected from methyl and ethyl; $R^3$ and $R^5$ are each independently selected from H, halo, methyl, nitro, cyano, amino, —CH=NOCH$_3$ and —NHCOOCH$_3$, and $R^4$ is selected from H, halo, amino, cyano, —CH=NOCH$_3$, —NHCOOCH$_3$, COOCH$_3$, and $(C_1-C_4)$ alkyl.

In an even more preferred embodiment of the method of the present invention, the compounds have the structural formula (II), wherein X is chloro, Y is H, $R^1$ is methyl, $R^2$ is ethyl, $R^3$ and $R^5$ are each independently selected from halo, methyl, cyano and —CH=NOCH$_3$, and $R^4$ is H, amino, methyl, or —CH=NOCH$_3$.

In another preferred embodiment of the method of the present invention, the compounds have the structural formula (I), wherein A is 3-pyridyl and the compounds have the structural formula:

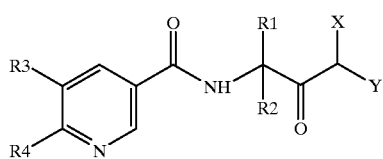

III wherein:

$R^1$ and $R^2$ are independently selected from H, $(C_1-C_6)$alkyl, halo$(C_1-C_6)$alkyl, $(C_2-C_6)$alkenyl, and $(C_2-C_6)$alkynyl, provided that at least one of $R^1$ and $R^2$ is other than H; $R^3$ and $R^4$, are each independently selected from H, halo, cyano, $(C_1-C_6)$alkyl, halo$(C_1-C_6)$alkyl, $(C_2-C_6)$ alkenyl, $(C_2-C_6)$alkynyl, $(C_1-C_6)$alkoxy, $(C_1-C_6)$ alkylthio, halo$(C_1-C_6)$alkoxy, nitro, —NR$^6$R$^7$, —CR$^8$=NOR$^9$, NHCOOR$^{10}$, —CONR$^{11}$R$^{12}$, and —COOR$^{13}$;

$R^6$, $R^7$, $R^8$, $R^9$, $R^{10}$, $R^{11}$, $R^{12}$, and $R^{13}$ are H or $(C_1-C_6)$ alkyl; and X and Y are each independently selected from H, halo, cyano, thiocyano, isothiocyano and $(C_1-C_6)$ alkylsulfonyloxy, provided that at least one of X and Y is other than H.

When $R^1$ and $R^2$ are different, optical enantiomers of the compounds of the present invention are possible due to the presence of an asymmetric carbon atom linking $R^1$ and $R^2$. It is known that many biologically active compounds have optical enantiomers, one of which is more active than the other. Similarly, for compounds used in the method of the present invention, the biological activity of one enantiomer may exceed that of the other enantiomer. In such cases, both enantiomers are within the scope of the present invention. The enantiomers are known as "S" enantiomers and "R" enantiomers. The term "S enantiomer" means that the four groups on the carbon to which $R^1$ and $R^2$ are attached, when ranked according to the set of sequence rules of the Cahn-Ingold-Prelog system (*Angew. Chem. Int. Ed. Engl.* 5, 385–415 (1966)), define the carbon as having an S configuration. The term "R enantiomer" means that the four groups form an R configuration.

The method of the present invention are useful in treating protozoal infections. Protozoans which may be controlled by the method of the present invention include but are not limited to Giardia species, Leishmania species, Entamoeba species, Toxoplasma species, Cryptosporidium species, and microsporidia species. The method of the present invention may be used to treat diseases caused by protozoans in animals, including humans, domestic animals such as cattle and pigs, and poultry.

The method of the present invention includes administering the effective compounds described herein to animals by any route appropriate to the condition to be treated. Physiologically acceptable acid addition salts of compounds described herein are also useful in treating disease. The term "physiologically acceptable acid addition salts" is intended to include any non-toxic organic or inorganic acid addition salts of basic forms of the compounds described herein. In general, compounds having basic groups may form acid addition salts. When several basic groups are present, mono- or poly-salts may be formed. For example compounds such as those containing a pyridine ring or an amino substituent, may be reacted with a physiologically acceptable acid, and the resulting acid addition salt may be administered. Suitable inorganic acids for use in preparing acid addition salts are well known to the art of pharmaceutical formulation and include hydrochloric, hydrobromic, hydroiodic, sulfuric, nitric, and phosphoric acids, and acid metal salts such as sodium monohydrogen orthophosphate and potassium hydrogen sulfate. Examples of organic acids which form suitable salts include mono, di, and tricarboxylic acids, such as acetic, glycolic, lactic, pyruvic, malonic, fumaric, benzoic, citric, maleic, tartaric, succinic, gluconic, ascorbic, sulfamic, oxalic, pamoic, hydroxymaleic, hydroxybenzoic, phenylacetic, salicylic, methanesulfonic, ethanesulfonic, 2-hydroxyethanesulfonic, benzenesulfonic, or 2-phenoxybenzoic acids or mixtures thereof. (See, for example Berge, et al., "Pharmaceutical Salts," in *J. Pharm. Sci.*, 66:1–19 (1977)). Acid addition salts may be prepared by standard techniques such as by dissolving the free base in aqueous or aqueous-alcohol solution or other suitable solvent containing the appropriate acid and isolating by evaporating the solution or by reacting the free base in an organic solvent in which case the salt separates directly or can be obtained by concentration of the solution. In general, acid addition salts are crystalline materials which are more soluble in water than the free base. As a specific example, the hydrochloride salt of compound 11 (described in Table X, below) may be prepared by dissolving the compound in anhydrous ethyl ether, bubbling in dry hydrogen chloride gas, filtering, and drying the resultant precipitate.

For pharmaceutical use, the compounds described herein may be taken up in pharmaceutically acceptable carriers, such as, for example, solutions, suspensions, tablets, capsules, ointments, elixirs and injectable compositions. Pharmaceutical preparations may contain from 0.1% to 99% by weight of active ingredient. Preparations which are in single dose form, "unit dosage form", preferably contain from 20% to 90% active ingredient, and preparations which are not in single dose form preferably contain from 5% to 20% active ingredient. As used herein, the term "active ingredient" refers to compounds described herein, salts thereof, and mixtures of compounds described herein with other pharmaceutically active compounds. Dosage unit forms such as, for example, tablets or capsules, typically contain from about 0.05 to about 1.0 g of active ingredient.

Suitable routes of administering the pharmaceutical preparations include oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that the preferred route of administration will depend upon the condition being treated and may vary with factors such as the condition of the recipient.

According to the method of the present invention, the effective compounds described herein may be administered alone or in conjunction with other pharmaceutically active compounds. It will be understood by those skilled in the art that pharmaceutically active compounds to be used in combination with the compounds described herein will be selected in order to avoid adverse effects on the recipient or undesirable interactions between the compounds. As used herein, the term "active ingredient" is meant to include compounds described herein when used alone or in combination with one or more additional pharmaceutically active compounds.

The amount of the compounds described herein required for use in the treatment or prophylaxis of protozoal infections will depend itter aclia on the route of administration, the age and weight of the animal (e.g. human) to be treated and the severity of the condition being treated. In general, a suitable dose for administration to man for the treatment of protozoal infections is in the range of 1.0 mg to 200.0 mg per kilogram bodyweight per day, for example from 5 mg/kg to 100 mg/kg, particularly 25 to 100 mg/kg. It will be appreciated that for administration to neonates, lower doses may be required.

For prophylactic treatment the compound of formula I or a physiologically acceptable salt thereof may also be given less frequently, e.g. as a single dose on alternate days, once or twice per week or once or twice per month. The dosage for prophylactic treatment will depend inter alia on the frequency of administration, and, where a depot preparation or controlled release formulation is used, the rate of release of the active ingredient. Thus for once-weekly administration a suitable prophylactic dose is in the range 0.5 to 100 mg/kg, e.g. 1.0 to 50 mg/kg, particularly 5 to 50 mg/kg.

While the compounds described herein may be administered alone to treat protozoal infections, it is preferable to administer them as pharmaceutical formulations. Useful formulations comprise one or more active ingredients and one or more pharmaceutically acceptable carriers. The term "pharmaceutically acceptable" means compatible with the other ingredients of the formulation and not toxic to the recipient. Useful pharmaceutical formulations include those suitable for oral, rectal, nasal, topical, vaginal or parenteral administration, as well as administration by naso-gastric tube. The formulations may conveniently be prepared in unit dosage form and may be prepared by any method known in the art of pharmacy. Such methods include the step of bringing the active ingredient into association with the carrier, which may constitute one or more accessory ingredients. In general, the formulations are prepared by uniformly bringing the active ingredients into association with liquid carriers or finely divided solid carriers or both, and then, if necessary, shaping the product.

Formulations suitable for oral admininstration may be used in discrete units such as capsules, cachets or tablets each containing a predetermined amount of active ingredient; as a powder or granules; as a solution or suspension in an aqueous or non-aqueous liquid; or as an oil-in-water or a water-in-oil liquid emulsion. The active ingredient may also be administered as a bolus or paste or may be contained within liposomes.

A tablet may be made by compression or molding, and may include one or more accessory ingredients. Compressed tablets may be prepared by compressing in a suitable machine the active ingredient in a free-flowing form such as powder or granules. Accessory ingredients with which the active ingredient may be mixed include one or more of the following: a binder such as povidone, gelatin, or hydroxypropylmethyl cellulose; a lubricant, inert diluent, preservative, disintegrant such as sodium starch glycolate, cross-linked povidone, or cross-linked sodium carboxymethylcellulose; surface active agent; or dispersing agent. Molded tables may be made by molding in a suitable machine a mixture of powdered active ingredient moistened with an inert liquid diluent. The tablets may be coated or scored and may be formulated so as to provide slow or controlled release of active ingredient therein, using, for example, hydroxypropylmethyl cellulose in proportions to provide the desired release profile.

A capsule may be filled with loose or compressed powdered active ingredient on an appropriate filling machine, optionally with one or more additives. Examples of suitable additives include binders such as povidone, gelatin, lubricants, inert diluents, and disintegrants, as described above for tablets. Capsules may also be formulated to contain pellets or discrete sub-units to provide controlled or slow release of active ingredient. This may be achieved, for example, by extruding and spheronizing a wet mixture of active ingredient with an extrusion agent such as microcrystalline cellulose. The spheroids thus produced may be coated with a semipermeable membrane of, for example, ethyl cellulose, to produce sustained release properties.

For topical administration the compounds are preferably applied as an ointment or cream containing the active ingredient in an amount of, for example, 0.075 to 20 weight percent, preferably 0.2 to 15 weight percent, and most preferably 0.5 to 10 weight percent. When formulated in an ointment, the active ingredient may be incorporated in either a paraffininc or water-miscible ointment base. Alternatively, the active ingredient may be formulated in a cream with an oil-in-water cream base or a water-in-oil base.

The aqueous phase of the cream base may include a polyhydric alcohol. A polyhydric alcohol is an alcohol having two or more hydroxyl groups such as, for example, propylene glycol, butane-1,3-diol, mannitol, sorbitol, glycerol, and polyethylene glycol and mixtures thereof. The amount of polyhydric alcohol will typically be about 30 weight percent. Topical formulations may include one or more compounds to enhance absorption or penetration of active ingredient through the skin or other affected areas. Examples of such dermal penetration enhancers include dimethylsulfoxide and related analogs.

The oily phase of the cream base may include other ingredients commonly used in the art, such as one or more emulsifiers, a fat or an oil or both a fat and an oil. Preferably, a hydrophilic emulsifier is included together with a lipophilic emulsifier which acts as a stabilizer. It is also preferred to include both an oil and a fat. Together the emulsifer with or without stabilizer make up an emulsifying wax, and the emulsifying wax together with the oil or fat make up an emulsifying ointment base which forms the oily dispersed phase of the cream formulation.

Emulsifiers and emulsion stabilizers suitable for use in formulations of the compounds used in the method of the present invention include cetostearyl alcohol, myristyl alcohol, glycerol monostearate and sodium lauryl sulphate. Examples of suitable commercially available emulsifiers include Tween® 60 polyoxyethylene (20) sorbitan monostearate and and Span® 80 sorbitan monooleate.

The choice of suitable oils or fats for the formulation depends upon desired properties. The cream should preferably be a non-greasy, non-staining and washable product with suitable consistency to avoid leakage from tubes or other containers. Straight- or branched-chain, mono- or di-basic alkyl esters such as, for example, di-isoadipate, isocetyl stearate, propylene glycol diester of coconut fatty acids, isopropyl myristate, decyl oleate, isopropyl palmitate, butyl stearate, or 2-ethylhexyl palmitate may be used. The esters may be used alone or in combination depending on the desired properties. Alternatively, relatively high-melting lipids such as white soft paraffin or liquid paraffin or other mineral oil may be used.

Formulations suitable for topical administration to the eye also include eye drops wherein the active ingredient is dissolved or suspended in a suitable carrier, such as an aqueous solvent for the active ingredient. The concentration of active ingredient is preferably from 0.5 percent to 20 percent by weight, more preferably from 0.5 percent to 10 percent, most preferably about 1.5 weight percent.

Formulations suitable for rectal administration may be in the form of a suppository with a suitable base comprising, for example, cocoa butter or higher fatty alcohol, triglycerides, or saturated fatty acids.

Formulations suitable for vaginal administration may be administered as pessaries, tampons, creams, gels, pastes, foams or spray fomulations containing appropriate carriers.

The active ingredient may also be formulated as a solution or suspension suitable for administration via a naso-gastric tube.

Formulations suitable for parenteral administration include aqueous and non-aqueous sterile injection solutions which may contain anti-oxidants, buffers, bacteriostats, and solutes which render the formulations isotonic with the blood of the recipient; and aqueous and non-aqueous sterile suspensions which may include suspending agents and thickening agents, liposomes, or other microparticulate systems designed to direct the active ingredient to blood components or one or more organs. The formulations may be in unit dose or multi dose containers such as, for example, sealed ampules and vials, and may be stored in a lyophilized condition requiring only the addition of a sterile liquid carrier, such as water suitable for injection, immediately prior to use. Injection solutions and suspensions may be prepared extemporaneously from sterile powders, granules, and tablets of the kind described herein.

Preferred unit dosage formulations are those containing a daily dose or unit, daily sub-dose, or an appropriate fraction thereof, of active ingredient.

The compounds described herein may also be formulated as long-acting depot preparations, which may be administered by intramuscular injection or by implantation e.g. subcutaneously or intramuscularly. Depot preparations may include, for example, suitable polymeric or hydrophobic materials, or ion-exchange resins. Such long-acting formulations are particularly useful for prophylactic use.

It should be understood that in addition to the ingredients particularly mentioned above, the formulations for use in the method of the present invention may include other agents conventional in the art, depending upon the mode of administration. For example, formulations suitable for oral administration may include flavoring agents.

The compounds described herein may also be used in accordance with the present invention in combination with other therapeutic agents, for example agents used in the treatment of immunocompromised patients, including antibacterial agents; antifungal agents; anticancer agents such as interferons e.g. alpha-interferon; antiviral agents such as azidothymidine; immunostimulants and immunomodulators. The compound of formula I may also be administered in combination or concurrently with anti-diarrhoeal agents such as loperamide hydrochloride and/or diphenoxylate hydrochloride, or with morphine sulfate. Oral rehydration therapy may also be carried out concurrently.

Compositions suitable for veterinary use include those adapted for oral, parenteral, and intrarumenal administration.

Compounds suitable for oral administration include drenches (oral liquid dosing), which may be solutions or suspensions; tablets, boluses, pastes, or in-feed preparations in the form of powders, granules or pellets.

Alternatively, veterinary compositions may be adapted to be administered parenterally by subcutaneous, intramuscular or intravenous injection of a sterile solution or suspension, by implantation or as an intramammary injection whereby a suspension or solution is introduced into the udder via the teat.

For intrarumenal injection, the compositions of the invention may be solutions or solid or microcapsule suspension. Typically the compositions are similar to the oral liquid preparations or parenteral preparations described herein. Such compositions are injected directly into the rumen, usually through the side of the animal, for example by a hypodermic syringe and needle or by an automatic injection device capable of giving single or multiple doses.

For veterinary administration the compound of formula I or a physiologically acceptable salt thereof is preferably formulated with one or more veterinarily acceptable carriers.

For oral administration, fine powders or granules may contain diluting agents, for example lactose, calcium carbonate, calcium phosphate, mineral carriers, etc., dispersing and/or surface active agents, for example polysorbates such as Tweens or Spans, and may be presented in a drench, in water or in a syrup, in a bolus, paste, or in a feed preparation, in capsules or sachets in the dry state or in a non-aqueous suspension, or in a suspension in water or syrup. Where desirable or necessary, preserving, suspending, thickening or emulsifying agents can be included. If intended for oral use, a bolus will be provided with retention means to inhibit regurgitation, for example it may be weighted with a heavy density material such as iron or tungsten or the like or may be retained by its shape, for example by wings which spring after administration. Boluses may contain disintegrating agents such as maize starch or calcium or sodium methyl celluloses, hydroxypropylmethylcellulose, guar based vegetable gums, sodium alginates or sodium starch glycolates; granulating or binding agents such as starch in the form of mucilage, starch derivatives, such as "Snow Flake", cellulose derivatives such as talc, calcium stearate, methyl cellulose, gelatin or polyvinylpyrrolidone; and/or lubricating agents, such as magnesium stearate or stearic acid.

For parenteral administration, the compounds may be presented in sterile injection solutions which may contain antioxidants or buffers, or as injectable suspensions. Suitable solvents include water, in the case of suspensions, and organic solvents such as dimethylformamide, dimethylacetamide, diethylacetamide, ethyl lactate, dimethylsulfoxide, alcohols, e.g. ethanol, glycols, e.g. ethylene glycol, propylene glycol, butylene glycol and hexamethylene glycol, polyethylene glycols having average molecular weights from about 90 to 7,500, glycerin formal glycofural, glycerol, isopropylmyristate, N-methylpyrrolidone, 2-pyrrolidone polyethylene glycoethers of tetrahydrofurfuryl alcohol and diethylene glycol, and fixed and neutral oils, for example fractionated coconut oil. Parenteral formulations may also contain isotonic agents.

For veterinary use the compound of formula I or a physiologically acceptable salt thereof may be employed together with other therapeutic agents used in the field of animal health, for example with anticoccidial or antitheilerial agents.

Particular compounds useful in the method of the present invention include those compounds listed in Tables 1–3.

In Table 1 are shown compounds having the structural formula (II).

TABLE 1

| Compound | R1 | R2 | R3 | R4 | R5 | x | y |
|---|---|---|---|---|---|---|---|
| 1 | $CH_3$ | $C_2H_5$ | Cl | $NH_2$ | Cl | Cl | H |
| 2 | $CH_3$ | $C_2H_5$ | CH=$NOCH_3$ | H | Cl | Cl | H |
| 3 | $CH_3$ | $C_2H_5$ | Br | H | $CH_3$ | Cl | H |
| 4 | $CH_3$ | $C_2H_5$ | Cl | H | Cl | Br | Br |
| 5 | $CH_3$ | $C_2H_5$ | Cl | H | Cl | Cl | H |
| 6 | $CH_3$ | $C_2H_5$ | CH=$NOCH_3$ | NH2 | Cl | Cl | H |
| 7 | $CH_3$ | $C_2H_5$ | Cl | H | Cl | SCN | H |
| 8 | $CH_3$ | $C_2H_5$ | Cl | H | Cl | NCS | H |
| 9 | $CH_3$ | $C_2H_5$ | Cl | F | Cl | Cl | H |
| 10 | $CH_3$ | $C_2H_5$ | Cl | $CH_3$ | Cl | Cl | H |
| 11 | $CH_3$ | $C_2H_5$ | F | F | F | Cl | H |
| 12 | $CH_3$ | $C_2H_5$ | F | H | F | Cl | H |
| 13 | $CH_3$ | $C_2H_5$ | Cl | H | Cl | Cl | H |
| 14 | $CH_3$ | $C_2H_5$ | Br | $NH_2$ | Br | Cl | H |

Table 2 lists compounds having the structural formula (III).

TABLE 2

| Compound | R1 | R2 | R3 | R4 | X | Y |
|---|---|---|---|---|---|---|
| 15 | $CH_3$ | $C_2H_5$ | Br | H | Cl | H |

Table 3 lists compounds having the structural formula (II), wherein $R^4$ and $R^5$ together form a fused ring.

TABLE 3

| Compound | R1 | R2 | R3 | R4R5 | x | y |
|---|---|---|---|---|---|---|
| 16 | $CH_3$ | $C_2H_5$ | Cl | —N=CH—O— | Cl | H |

Methods used in preparing compounds listed in Tables 1–3
Compounds 3, 4, 5, 7, 8, 9, 11, 12 and 13 in Table 1:

Compounds 3, 4, 5, 7, 8, 9, 11, 12 and 13 in Table 1 were prepared according to synthetic methods described in U.S. Pat. No. 4,822,902, columns 5–8 and 11–17.

Compound 2 in Table 1:

Compound 2 in Table 1 was prepared according to synthetic methods described in U.S. Pat. No. 5,254,584, columns 10–14.

Compound 10 in Table 1:

Compound 10 was prepared according to synthetic methods described in U.S. Pat. No. 5,304,572, columns 4–8.

Compounds 1 and 14 in Table 1:

Compounds 1 and 14 were prepared using conventional synthesis techniques, as described for example in U.S. Pat. No. 4,863,940, columns 5–7, from appropriate benzoic acids or benzoyl chlorides. Thus, compounds 1 and 14 were prepared from 4-amino-3,5-dichlorobenzoylchloride and 4-amino-3,5-dibromobenzoylchloride, respectively.

Compound 6 in Table 1:

Compound 6 was prepared by reaction of the benzoyl chloride IV, in which $R^3$ is Cl, $R^1$ is $NH_2$ and $R^5$ is $CHNOCH_3$, with the α-amino-α'-chloroketone derivative V, in which $R^1$ is methyl and $R^2$ is ethyl, as illustrated in Scheme A:

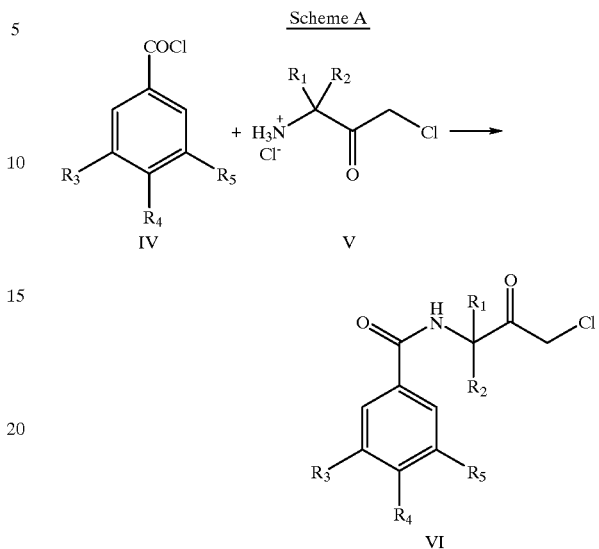

The starting benzoyl chloride used to prepare compound 6 was prepared as indicated below in scheme B.

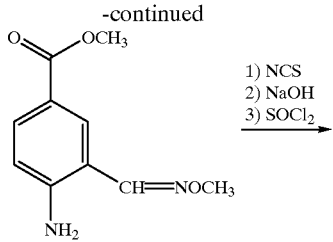

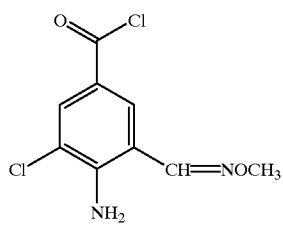

Compound V was prepared by treating the acetylenic amine (VII) with trifluoracetic anhydride in the presence of a solvent such as methylene chloride, chloroform, ethyl ether, or water and a base such as triethylamine, sodium carbonate, sodium bicarbonate, or sodium hydroxide to yield the acetylenic amide VIII:

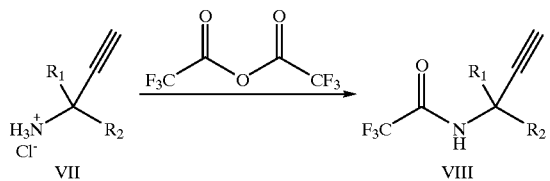

Treatment of the acetylenic amide VIII with chlorine or a chlorine source at a temperature of from −78° C. to 0° C. in the presence of a solvent such as methylene chloride or chloroform yielded the intermediate oxazoline (IX). The oxazoline IX was readily hydrolyzed under acidic conditions using an acid such as hydrochloric acid or sulfuric acid with a solvent such as methanol or tetrahydrofuran at a temperature of from 40° C. to 60° C., yielding the α-amino-α', α'-dichloroketone (X).

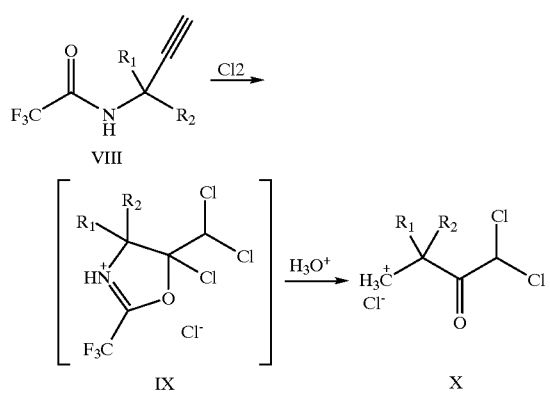

Selective catalytic dehalogenation of X yielded the respective α-amino-α'-chloroketone derivative V:

a) Preparation of methyl 3-methyl-4-nitrobenzoate.

In a 5-liter three-necked round-bottomed flask equipped with a reflux condenser, overhead stirrer and gas inlet, was placed 300 g of 3-methyl-4-nitrobenzoic acid and 3 l of methanol. To the resulting well-stirred solution was bubbled in 20.8 g of hydrogen chloride and the resulting mixture was refluxed for 3 hours. The reaction mixture was cooled to room temperature and allowed to stand overnight. The expected methyl 3-methyl-4-nitrobenzoate precipitated as light yellow crystals, which were collected by suction filtration yielding after drying 259.3 g. This solid was used as such in the next step.

b) Preparation of methyl 3-bromomethyl-4-nitrobenzoate.

In a 5-liter three-necked round-bottomed flask equipped with a reflux condenser, overhead stirrer, addition funnel and nitrogen inlet, was placed 220 g of methyl 3-methyl-4-nitrobenzoate, 2 l of anhydrous carbon tetrachloride and 4 g of benzoyl peroxide. To the resulting solution, irradiated with a 275 watt UV light, was added 198 g of bromine dropwise over a period of 2 hours at reflux. After the addition was complete the reaction mixture was refluxed for an additional 60 hours. The reaction mixture was cooled to room temperature. The solid which formed was separated by suction filtration. This solid (159.1 g) consisted of the expected methyl 3-bromomethyl-4-nitrobenzoate with minor amounts of the starting material. The mother liquors together with another 220 g of methyl 3-methyl-4-nitrobenzoate and 4 g of benzoyl peroxide were returned to the flask and treated with 198 g of bromine as described above. After the addition was complete the reaction mixture was refluxed another 96 hours, cooled to room temperature and the resulting solid separated by filtration yielding another 252 g of methyl 3-bromomethyl-4-nitrobenzoate. The solids were combined yielding a total of 411.1 g of methyl 3-bromomethyl-4-nitrobenzoate with minor amounts of the starting methyl 3-methyl-4-nitrobenzoate and methyl 3-dibromomethyl-4-nitrobenzoate. This solid was used as such in the next step.

c) Preparation of methyl 3-acetoxymethyl-4-nitrobenzoate.

In a 5-liter three-necked round-bottomed flask equipped with a reflux condenser, overhead stirrer and nitrogen inlet, was placed 411 g of the previously prepared methyl 3-bromomethyl-4-nitrobenzoate, 441 g of anhydrous potassium acetate and 2 l of glacial acetic acid. The resulting mixture was refluxed for 4 hours, cooled to room temperature and stirred overnight. Th e solvent was removed in a rotary evaporator and the resulting light yellow solid treated with a mixture of 2 l of ethyl acetate and 1 l of water. The organic phase was separated, washed with water (3×400 mL), brine (1×400 mL) (hied over anhydrous magnesium sulfate and the solvent removed using a rotary evaporator. The crude reaction mixture was triturated with hexane and filtered Yielding 318 g of the expected methyl 3-acetoxymethyl-4-nitrobenzoate. This compound was used as such in the next step.

d) Preparation of methyl 3-hydroxymethyl-4-nitrobenzoate.

In a 5-liter three-necked round-bottomed flask equipped with a reflux condenser, overhead stirrer and nitrogen inlet, was placed 318 g of the previously prepared methyl 3-acetoxymethyl-4-nitrobenzoate and 3.2 l of anhydrous methanol. To the resulting solution was bubbled in 40 g of hydrogen chloride and the resulting mixture was refluxed for 3 hours. After cooling to room temperature the solvent was removed using a rotary evaporator yielding 273 g of methyl 3-hydroxymethyl-4-nitrobenzoate as a yellow solid containing traces of methanol, which was used as such in the next step.

e) Preparation of methyl 3-formyl-4-nitrobenzoate.

In a 5-liter four-necked round-bottomed flask 1.5 l of methylene chloride was cooled to −78° C. Oxalyl chloride (164 g, 1.29 moles) was added slowly, followed by dropwise addition of 202 g (2.59 moles) of dry dimethylsulfoxide in 125 mL of methylene chloride, keeping the temperature below −70° C. After the addition was complete the reaction mixture was stirred at −78° C. for 30 minutes and 273 g (1.29 moles) of previously prepared methyl 3-hydroxymethyl-4-nitrobenzoate dissolved in 250 mL of methylene chloride was added dropwise. The reaction mixture was stirred an additional 30 minutes. Triethylamine (392 g 3.88 moles) in 125 mL of methylene chloride was added dropwise keeping the temperature below −65° C. The reaction mixture was warmed up slowly to room temperature and stirred overnight. The solvent was removed using a rotary evaporator and the resulting solid treated with a mixture of 2 l of ethyl acetate and 1 l of water. The organic phase was separated, filtered through diatomaceous earth, and washed sequentially with dilute aqueous hydrochloric acid (2×250 mL), water (2×250 mL), saturated aqueous sodium bicarbonate (2×250 mL), water (2×200 mL), brine (1×200 mL) and dried over anhydrous magnesium sultate. The solvent was removed using a rotary evaporator. The crude reaction mixture was triturated with hexane and filtered yielding 234.1 g of the expected methyl 3-formyl-4-nitrobenzoate as a yellow solid. This compound was used as such in the next step.

f) Preparation of methyl 3-methoxyiminomethyl-4-nitrobenzoate.

To a well stirred mixture of 195 g of methyl 3-formyl-4-nitrobenzoate, 1 l methylene chloride and 370 mL of water was added sequentially 77.6 g of methoxylamine hydrochloride, 76.2 g of sodium acetate and 6.8 g of tetra-n-butylammonium hydrogen sulfate. The resulting mixture was stirred overnight at room temperature, then diluted with 2 l of ethyl ether. The organic phase was separated and washed sequentially with water (1×500 mL), 2% aqueous hydrochloric acid (2×500 mL), water (2×250 mL), and brine (1×250 mL); then dried over anhydrous magnesium sulfate. The solvent was removed using a rotary evaporator yielding 218.6 g of the expected methyl 3-methoxyiminomethyl-4-nitrobenzoate as a reddish oil that solidified upon standing, and which was used as such in the next step.

g) Preparation of methyl 4-amino-3-methoxyiminomethylbenzoate

In a 5-liter three-necked round-bottomed flask was placed 0.9 l of 5% aqueous acetic acid and 157 g (2.8 moles) of iron. To the resulting well-stirred mixture was added 166.6 g (0.7 moles) of the previously prepared methyl 3-methoxyiminomethyl-4-nitrobenzoate dissolved in 0.9 l of ethyl acetate followed by dropwise addition of 0.9 l of acetic acid while keeping the temperature below 35° C. The resulting mixture was stirred at 35° C. for 30 minutes and filtered through diatomaceous earth. The filtrate was poured into 5 l of water. The aqueous phase was separated and washed with ethyl ether (2×500 mL). The combined organic layers were washed sequentially with water (4×500 mL), saturated aqueous sodium bicarbonate (2×500 mL), water (2×500 mL), and brine (1×400 mL). The organic layer was dried over anhydrous magnesium sulfate and the solvent removed using a rotary evaporator yielding 130 g of the expected methyl 4-amino-3-methoxyiminomethylbenzoate.

h) Preparation of methyl 4-amino-3-chloro-5-methoxyiminomethylbenzoate.

In a 2-liter three-necked round-bottomed flask was placed 106 g (0.51 moles) of the previously prepared 4-amino-3-methoxyiminomethylbenzoate and 500 mL of acetonitrile. The resulting mixture was heated at 70° C. and 75.2 g (0.56 moles) of N-chlorosuccinimide was added portionwise while keeping the temperature below 80° C. After the addition was complete the reaction mixture was refluxed for 1 hour. The reaction mixture was cooled to room temperature and the solvent eliminated in a rotary evaporator. The crude product was dissolved in 5 l of ethyl acetate. The organic solution was washed with water (3×500 mL) and then brine, dried over magnesium sulfate. The reaction mixture was concentrated in a rotary evaporator to a slurry, triturated with hexane and filtered yielding the expected methyl 4-amino-3-chloro-5-methoxyiminomethylbenzoate as a yellow solid. This reaction was repeated using the same amounts yielding a total of 210.5 g of methyl 4-amino-3-chloro-5-methoxyiminomethylbenzoate, which was used as such in the next step.

i) Preparation of 4-amino-3-chloro-5-methoxyiminomethylbenzoic acid.

In a 5-liter three-necked round-bottomed flask was placed 210 g (0.86 moles) of the previously prepared 4-amino-3-chloro-5-methoxyiminomethylbenzoate, 1.7 l of methanol and 462 g (1.73 moles) of 15% aqueous sodium hydroxide. The resulting mixture was refluxed for 3 hours, after which the reaction mixture was stirred overnight at room temperature. The reaction mixture was concentrated using a rotary evaporator. The crude reaction mixture was dissolved in 2 l of water. The resulting aqueous solution was washed once with 500 mL of ethyl acetate, cooled in an ice bath and acidified to pH=2 with concentrated hydrochloric acid. The expected 4-amino-3-chloro-5-methoxyiminomethylbenzoic acid precipitated as a light yellow solid which was separated by suction filtration. The filter cake was washed with a 1:2 mixture of ethyl ether and hexane yielding after drying 185.2 g (94% yield).

j) Preparation of 4-amino-3-chloro-5-methoxyiminomethylbenzoyl chloride.

In a 5-liter three-necked round-bottomed flask was placed 180 g of the previously prepared 4-amino-3-chloro-5-methoxyiminomethylbenzoic acid, 2 l of toluene, 3 mL of dimethylformamide and 104 g (64 mL) of thionyl chloride. The resulting mixture was heated at 70° C. for 2 hours, filtered while hot and the solvent removed using a rotary evaporator yielding 178.1 g of the expected 4-amino-3-chloro-5-methoxyiminomethylbenzoyl chloride.

k) Preparation of 3-amino-1-chloro-3-methyl-2-pentanone hydrochloride (Compound V, wherein $R_1$ is methyl and $R_2$ is ethyl)

i) Preparation of N-[3-(3-methyl-1-pentynyl)] trifluoroacetamide

In a 3 liter, four-necked, round-bottomed flask fitted with a mechanical stirrer, nitrogen inlet and thermometer was placed 234 grams (g) (1.75 mole) of 3-amino-3-methyl-1-pentyne hydrochloride and 1,000 mL of methylene chloride. To the resulting well-stirred mixture was added slowly 354 g (3.51 mole) of triethylamine (TEA) dropwise, keeping the temperature below 30° C. After the addition was completed, the reaction mixture was stirred 120 minutes followed by dropwise addition of 334.5 g (1.59 mole) of trifluoroacetic anhydride dissolved in 500 mL of methylene chloride at such a rate to keep the reaction temperature at 0° C. After the addition was completed the reaction mixture was stirred at room temperature overnight and concentrated in vacuo. The resulting slurry was washed with ethyl ether. The ethyl ether layer was washed sequentially with water, saturated aqueous sodium bicarbonate and brine, dried over anhydrous magnesium sulfate, treated with activated charcoal, and filtered through Celite® filter agent (available from Aldrich Chemical Company, St. Louis, Mo.). The solvent was eliminated under reduced pressure. The resulting crude product was treated with cold pentane, filtered, and dried yielding 255.5 g (83%) of the expected N-[3-(3-methyl-1-pentynyl)] trifluoroacetamide as a white solid.

ii) Preparation of 5-chloro-5-(dichloromethyl)-4-ethyl-4-methyl-2-trifluoromethyloxazoline hydrochloride:

In a 5 L, four-necked, round-bottomed flask fitted with a mechanical stirrer, a thermometer, and a gas inlet was dissolved 255.5 g (1.32 mole) of N-[3-(3-methyl-1-pentynyl)]trifluoroacetamide in 4,000 mL of methylene chloride. The resulting mixture was cooled to −30° C. and 235 g of chlorine was bubbled in over a 2 hour period. When the addition was completed the reaction mixture was stirred at −30° C. during 30 minutes and warmed to room temperature. The crude reaction mixture was evaporated in the rotary evaporator yielding the expected 5-chloro-5-(dichloromethyl)-4-ethyl-4-methyl-2-trifluoromethyloxazoline hydrochloride which was used as such in the next step.

iii) Preparation of 3-amino-1,1-dichloro-3-methyl-2-pentanone hydrochloride:

The 5-chloro-5-(dichloromethyl)-4-ethyl-4-methyl-2-trifluoromethyloxazoline hydrochloride prepared in the preceding step was dissolved in 1800 mL of methanol, 72 mL of water, and 190 mL of concentrated hydrochloric acid, warmed to 50° C., and stirred at that temperature overnight. The crude reaction mixture was cooled and poured into an ice/water/ethyl ether mixture. The phases were separated and the ether layer was extracted once with water. The ether was saved (organic I). The combined aqueous layers were washed once with ethyl ether, and the organic layer was combined with organic I (organic II). The aqueous layer was neutralized with saturated aqueous sodium bicarbonate and extracted twice with ethyl ether. The combined ether layers were washed with water, brine, dried over anhydrous magnesium sulfate, treated with activated charcoal, and filtered through Celite® filter agent. To the resulting colorless solution was bubbled in anhydrous hydrogen chloride keeping the temperature below 20° C. The resulting white solid was filtered and dried yielding 124.8 g of the expected 3-amino-1,1-dichloro-3-methyl-2-pentanone hydrochloride as a white solid. The ethyl ether filtrate was combined with organic II and concentrated in vacuo; the resulting residue (150 g) was taken in a mixture of methanol/water/concentrated hydrochloric acid and heated at 50° C. over the weekend. The previously described workup yielded another 51 g of 3 -amino-1,1-dichloro-3-methyl-2-pentanone hydrochloride. The total amount obtained was 175.8 g (61% yield).

iv) Preparation of 3-amino-1-chloro-3-methyl-2-pentanone hydrochloride:

In a 2 L Parr™ bottle was placed 41 g of 3-amino-1,1-dichloro-3-methyl-2-pentanone hydrochloride, 0.8 g of 10% palladium over charcoal, and 400 mL of ethanol. The resulting mixture was shaken in a Parr™ apparatus at 50 psi for 3 hours. The crude reaction mixture was filtered through Celite® filter agent and evaporated in vacuo yielding a viscous oil, which was taken in 300 to 400 mL of ethyl acetate and stirred at room temperature for several hours. The expected 3-amino-1-chloro-3-methyl-2-pentanone hydrochloride crystallized as a white solid; 300 mL of hexane was added to the resulting suspension and filtered yielding 34 g (98%) of the expected 3-amino-1-chloro-3-methyl-2-pentanone hydrochloride.

The reaction was repeated starting with 41 g; 41 g; and 51 g of 3-amino-1,1-dichloro-3-methyl-2-pentanone hydrochloride yielding a total of 132.1 g (90% overall yield) of 3-amino-1-chloro-3-methyl-1-pentanone hydrochloride.

l) Preparation of 4-amino-3-chloro-5-methoxyiminomethyl-N-(3-chloro-1-ethyl-1-methyl-2-oxopropyl)benzamide (compound 6).

In a 5-liter three-necked round bottomed flask was placed 93 g of 3-amino-1-chloro-3-methyl-2-pentanone hydrochloride and 885 mL of water. To the resulting solution were added 138.6 g of sodium bicarbonate followed by 500 mL of ethyl acetate. To the resulting well-stirred mixture was added 123.5 g of 4-amino-3-chloro-5-methoxyiminomethylbenzoyl chloride dissolved in 1000 mL of ethyl acetate at room temperature over a period of 50 minutes. After the addition was complete the reaction mixture was stirred at room temperature for 1 hour. The two phases were separated and the organic layer was washed with water (2×500 mL) , brine (1×500 mL), dried over anhydrous magnesium sulfate and the solvent eliminated in a rotary evaporator yielding the crude product as a brown oil. This oil was passed through a short silica gel column using methylene chloride as elution solvent. Evaporation of the solvent yielded 133.3 g of the expected 4-amino-3-chloro-5-methoxyiminomethyl-N-(3-chloro-1-ethyl-1-methyl-2-oxopropyl)benzamide as an off-white solid (mp 140–141° C.).

Compound 15 in Table 2:

Compound 15 in Table 2 was prepared according to synthetic methods described in U.S. Pat. No. 4,863,940.

Compound 16 in Table 3:

Compound 16 was prepared by reaction of the corresponding aromatic derivative (IV), in which $R_3$ is chloro and $R_4$ and $R_5$ together form a fused ring, with 3-amino-1-chloro-3-methyl-2-pentanone hydrochloride (compound V in which $R_1$ is methyl and $R_2$ is ethyl) as illustrated above in Scheme A:

To prepare the aromatic portion of compound 16, the 6-carboxy benzoxazole derivative XI was prepared from the corresponding 2-amino phenol derivative by procedures known in the art and described in, for example, E. C. Taylor, ed., *The Chemistry of Heterocyclic Compounds*, vol. 47, John Wiley & Sons, 1987 "Synthesis of Fused Heterocycles", edited by G. P. Ellis; p. 50, part I and pp. 713–714 part II). This procedure is set forth below:

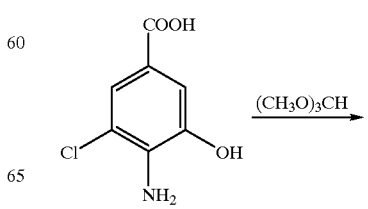

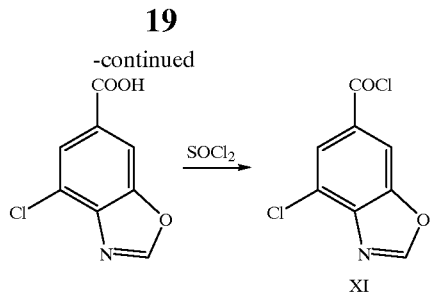

XI

To prepare compound 16, 6-carboxy-4-chloro-1,3-benzoxazole was prepared from 4-amino-5-chloro-3-hydroxy benzoic acid by treatment with trimethylorthoformate. 6-Carboxy-4-chloro-1,3-benzoxazole was first treated with thionyl chloride to give the acid chloride. The acid chloride was treated with 3-amino-1-chloro-3-methyl-2-pentanone hydrochloride in the presence of triethylamine to yield compound 16.

The following examples are provided in order to illustrate the method of the present invention.

EXAMPLE 1

Testing Against the Intestinal Flagellate *Giardia lamblia*

Compounds were tested for in vitro growth inhibitory activity against *G. lamblia* using methods described in Katiyar, S. K. and Edind, T. D., Antimicrobial Agents and Chemotherapy, vol. 35, pp. 2198–2202 (1991). EC50 values for test compounds, expressed in parts per million (ppm), were calculated from dose response curves and are presented in Table 4. As used herein, the terminology "EC50" means the concentration of test compound required to inhibit growth by 50% are compared to a control lacking the test compound. Metronidazole was included as a standard in the tests for comparative purposes.

TABLE 4

Growth inhibitory activity towards *Giardia lamblia*

| Compound | EC50 (ppm) *Giardia lamblia* |
|---|---|
| 1 | 0.06 |
| 2 | 0.03 |
| 3 | 0.06 |
| 4 | 0.3 |
| 5 | 0.02 |
| 6 | 0.009 |
| 7 | 0.05 |
| 8 | 0.2 |
| 9 | 0.03 |
| 10 | 0.06 |
| 15 | 0.2 |
| 16 | 2.0 |
| Metronidazole | 0.7 |

EXAMPLE 2

Testing Against the Blood/Tissue-Dwelling Flagellate *Leishmania major*

Compounds were tested for in vitro growth inhibitory activity against *L. major* promastigotes using methods described in Katiyar, S. K. and Edlind, T. D., Antimicrobial Agents and Chemotherapy, vol. 35, pp. 2198–2202 (1991). EC50 values for test compounds were calculated from dose response curves and are presented in Table 5.

TABLE 5

Growth inhibitory activity towards *Leishmania major*

| Compound | EC50 (ppm) *Leishmania major* |
|---|---|
| 1 | 0.2 |
| 2 | 0.03 |
| 3 | 0.2 |
| 4 | 0.2 |
| 5 | 0.06 |
| 6 | 0.6 |
| 7 | 0.6 |
| 8 | 0.7 |
| 9 | 0.1 |
| 10 | 0.2 |
| 15 | 0.7 |
| 16 | 7 |

EXAMPLE 3

Testing Against the Intestinal Amoeba *Entamoeba histolytica*

Compounds were tested for in vitro growth inhibitory activity against *E. histolytica* using methods described in Katiyar, S. K. and Edlind, T. D., Antimicrobial Agents and Chemotherapy, vol. 35, pp. 2198–2202 (1991). EC50 values for test compounds were calculated from dose response curves and are presented in Table 6. Metronidazole was included as a standard in the test for comparative purposes.

TABLE 6

Growth inhibitory activity towards *Entamoeba histolytica*

| Compound | EC50 (ppm) *Entamoeba histolytica* |
|---|---|
| 1 | 38 |
| 2 | 12 |
| 3 | 16 |
| 10 | 6 |
| 15 | 20 |
| Metronidazole | 0.5 |

EXAMPLE 4

Testing Against the Ciliate *Tetrahymena pyriformis* and the Apicomplexa *Toxoplasma gondii* and *Cryptosporidium parvum*

Compounds were evaluated for in vitro growth inhibitory activity against the ciliate *Tetrahymena pyriformis*, which was used as an indicator organism for the Apicomplexia since by several criteria the ciliates and Apicomplexa are closely related (Edlind T. D. et al., Mol. Phylogenet. Evol. vol. 5, pp. 359–367, 1996). *T. pyriformis* (ATCC strain 30005) was grown in 1 ml ATCC medium 357 at 25° C. in 4 ml polyallomer culture tubes without shaking. Compounds were dissolved in dimethylsufoxide (DMSO) and added to the cultures (containing 3,000 cells/ml) such that the final DMSO concentration was 0.1–0.3%. After 24 hours, cell numbers were determined with a hemocytometer, and EC50 values were estimated from dose-response curves. The results are presented in Table 7. The dinitroanilines trifluralin, pendimethalin, and oryzalin which have in vitro activity against the Apicomplexa *Toxoplasma gondii*

(Stokkermans et al,. Exp. Parasitol. vol. 84, pp. 355–370, 1996) and *Cryptosporidium parvum* (Arrowood et al., FEMS Microbial. Lett., vol. 136, pp. 245–249, 1996) were tested for comparison.

TABLE 7

Growth inhibitory activity towards *Tetrahymena pyriformis*

| Compound | EC50 (ppm) Tetrahymena pyriformis |
|---|---|
| 1 | 0.02 |
| 2 | <0.01 |
| 3 | <0.01 |
| 4 | 0.1 |
| 5 | 0.003 |
| 6 | 0.02 |
| 7 | 0.07 |
| 8 | 0.07 |
| 9 | 0.004 |
| 10 | 0.004 |
| 15 | <0.01 |
| 16 | 0.6 |
| oryzalin | 0.4 |
| pendimethalin | 2 |
| trifluralin | >6 |

The high activities of the test compounds against *T. pyriformis* (Table 7) encouraged the testing of selected compounds against *Toxoplasma gondii* and *Cryptosporidium parvum*.

Compounds were tested for it vitro growth inhibitory activity against *Toxoplasma gondii* replication in L929 (L929-ATCC CCL 1, mouse connective tissue) or HFF (human foreskin fibroblast) host cells using the [$^3$H]-uracil incorporation technique as follows. Host cells were grown in 96-well flat-bottom microtiter plates at 37° C in a 5% carbon dioxide environment in modified Eagle's medium containing penicillin, streptomycin and 10% fetal equine serum. Wells containing a homogeneous confluent monolayer of host cells were infected with *T. gondii* tachyzoites at a ratio of 3 parasites per cell (approximately 6×10$^4$ tachyzoites per well containing 100 μl of medium). Solutions of test compounds were prepared in DMSO and diluted into growth medium to give a series of concentrations such that the final DMSO concentration was <1%. Two hours post infection, the cultures were washed to remove free parasites and the various dilutions of test compound were added. Cells were subsequently collected at 24, 48 and 72 hours. Four hours prior to each harvesting 50 Al of [$^3$H]-uracil (1 μCi) was added. Cells were collected using a cell harvester and incorporated radioactivity was measured using a scintillation counter.

Cytotoxicity of the test compounds towards host cells was determined using the Cell Titer 96™ it (Promega Corporation, Madison, Wis.) as follows. Cells were seeded at a concentration of 5×10$^3$ cells per well containing 100 μl of medium in 96-well flat-bottom microtiter plates and incubated at 37° C. in a 5% carbon dioxide environment for 4 hours. Dilutions of the test compounds prepared as described above were then added, and incubation continued for 24, 48 or 72 hours. Four hours before each of these time points the growth medium containing test compound was replaced with 100 μl of fresh medium followed by addition of 16 μl of the kit dye solution. After incubation at 37° C. for another 4 hours, 100 μl of the kit solubilization/stop solution was added to each well, the contents of the wells were mixed and the plates kept 1 hour at room temperature. The plates were then read spectrophotometrically in a plate reader at a wavelength of 570 nm. The effects of test compounds on growth of *T. gondii* and on growth of the host cells (values in parenthesis) are presented in Tables 8 and 9 with the extent of growth in the presence of the test compound expressed as a percentage of that in controls without test compound. Atovaquone was included in the test as a standard. Test compounds showed greater growth inhibitory activity towards *T. gondii* than towards the host cells.

TABLE 8

Growth inhibitory activity towards *T. gondii* in L929 host cells

| Compound | Concn. (μg/ml) | % Inhibition 24 hours | 48 hours | 72 hours |
|---|---|---|---|---|
| 1 | 0.5 | 7.8 (1.5) | 80.4 (11.6) | 95.4 (31.3) |
| 1 | 5.0 | 10.8 (19.7) | 75.5 61.8) | 78.2 (81.1) |
| 5 | 0.5 | 39.2 (0) | 64.7 (0) | 44.1 (0) |
| 5 | 5.0 | 3.3 (5.8) | 69.2 (66.8) | 84.0 (91.2) |
| 9 | 0.5 | 29.0 (6.3) | 86.3 (0) | 90.9 (8.5) |
| 9 | 5.0 | 28.2 (20.2) | 77.3 (65.2) | 95.6 (90.4) |
| 10 | 0.5 | 0 (3.7) | 0 (0) | 2.3 (2.2) |
| 10 | 5.0 | 20.5 (2.8) | 80.5 (0) | 90.4 (3.5) |
| 10 | 25.0 | 19.6 (2.2) | 86.5 (4.5) | 98.0 (7.6) |
| 11 | 5.0 | 21.5 (0) | 80.1 (5.5) | 95.4 (36.9) |
| 11 | 25.0 | 25.6 (22.6) | 66.1 (60.1) | 73.6 (89.6) |
| 12 | 0.5 | 42.0 (8.0) | 77.6 (0) | 59.0 (0) |
| 12 | 5.0 | 2.8 (18.9) | 55.0 (66.8) | 86.2 (88.0) |
| 13 | 0.5 | 11.6 (7.5) | 33.2 (0) | 0 (0) |
| 13 | 5.0 | 11.4 (18.7) | 83.9 (56.2) | 88.5 (76.6) |
| 14 | 0.5 | 29.3 (8.9) | 79.8 (0) | 84.9 (0) |
| 14 | 5.0 | 6.9 (21.8) | 61.2 (58.7) | 79.7 (77.6) |
| Atovaquone | 0.05 | 80.9 (0) | 0 (0) | 0 (0.2) |
| Atovaquone | 0.5 | 85.2 (14.3) | 99.0 (15.0) | 98.4 (44.4) |
| Atovaquone | 5 | 80.3 (20.0) | 100.0 (54.1) | 97.8 (78.1) |

TABLE 9

Growth inhibitory activity towards *T. gondii* in HFF host cells

| Compound | Concn. (μg/ml) | % Inhibition 24 hours | 48 hours | 72 hours |
|---|---|---|---|---|
| 1 | 0.5 | 47.6 (1.6) | 96.1 (0) | 91.3 (1.4) |
| 1 | 5.0 | 88.0 (14.7) | 99.3 (13.5) | 99.2 (47.6) |
| 5 | 0.5 | 55.9 (0) | 97.6 (5.3) | 80.2 (0) |
| 5 | 5.0 | 89.0 (8.0) | 100.0 (21.1) | 99.6 (39.6) |
| 9 | 0.5 | 58.7 (1.1) | 77.6 (1.1) | 0 (0) |
| 9 | 5.0 | 74.3 (2.4) | 97.0 (21.3) | 96.3 (6.3) |
| 10 | 0.5 | 2.3 (0) | 2.1 (0) | 6.3 (3.0) |
| 10 | 5.0 | 8.8 (1.4) | 1.4 (7.6) | 0 (3.5) |
| 10 | 25.0 | 63.4 (6.7) | 95.7 (9.3) | 97.3 (4.8) |
| 11 | 5.0 | 73.4 (2.1) | 98.4 (6.1) | 97.7 (0) |
| 11 | 25.0 | 91.9 (17.5) | 98.8 (20.0) | 97.7 (50.1) |
| 12 | 0.5 | 53.4 (4.6) | 95.3 (5.4) | 91.6 (0) |
| 12 | 5.0 | 84.4 (7.7) | 97.3 (29.1) | 998.0 (41.3) |
| 13 | 0.5 | 72.3 (3.4) | 28.1 (9.9) | 0 (2.0) |
| 13 | 5.0 | 93.0 (16.0) | 98.2 (41.3) | 97.8 (53.2) |
| 14 | 0.5 | 63.9 (4.1) | 96.1 (3.7) | 77.8 (0) |
| 14 | 5.0 | 87.4 (5.8) | 99.7 (31.8) | 99.1 (53.6) |
| Atovaquone | 0.05 | 1536 (0) | 50.5 (0) | 89.4 (0) |
| Atovaquone | 0.5 | 98.3 (0) | 77.8 (9.6) | 99.8 (1.4) |
| Atovaquone | 5 | 95.5 (6.2) | 99.8 (31.1) | 100.0 (28.1) |

Compounds were tested for in vitro growth inhibitory activity against *C. parvum* grown in host MDBKF5D2 cells and for toxicity towards the host cells as follows. Solutions of test compounds in DMSO were prepared at 50, 5, 0.5 and 0.05 mM, and diluted into Dulbecco's Modified Eagle Medium to give concentrations of 100, 10, 1 and 0.1 μM and a DMSO concentration of 0.2%. To test for toxicity towards the host cells, the media containing test compound (200 μl) were introduced into two wells of a 96 well microtiter plate containing confluent MDBKF5D2 cell monolayers and two wells without monolayers, and incubated at 37° C. in an 8% carbon dioxide environment. After 48 hours, the tetrazolium salt MTS (Owen's solution) and phenazine methosulfate were added to each well at concentrations of 333 μg/ml and 25 μM, respectively. The plate was returned to the incubator in the dark to develop for 2 hours, then 100 μl of each supernatant was transferred to a new microtiter plate and read spectrophotometrically in a plate reader at a wavelength of 490 nm. Percent toxicity was calculated by subtracting the mean optical density (OD) of the drug supernatants from the OD of medium control supernatants (no drug), dividing by the OD of the medium control, and multiplying by 100. To test for growth inhibitory activity against C. parvum, $3 \times 10^4$ oocysts per well were incubated in mentioned concentrations of each drug at 37° C. (8% $CO_2$) on confluent MDBKF5D2 cell monolayers in 96 well microtiter plates. After 48 hours, the level of infection in each well was determined by means of an immunofluorescence assay. Percent inhibition of growth was calculated by subtracting the mean parasite count in the wells containing test compound from the mean parasite count in the medium control wells (no test compound), dividing by the mean parasite count in the medium control wells, and multiplying by 100. The effects of test compounds on growth of C. parvum and their toxicity towards the host cells are presented in Table 10. Paromomycin was included in the test as a standard.

TABLE 10

Growth inhibitory activity towards *Cryptosporidium parvum*

| Compound | Concn. (μM) | % Inhibition | Cytotoxicity |
| --- | --- | --- | --- |
| 1 | 0.1 | 23.1 | 0 |
|  | 1.0 | 29.2 | 0 |
|  | 10 | 34.2 | 19.9 |
|  | 100 | 81.1 | 35.7 |
| 5 | 0.1 | 10.0 | 18.8 |
|  | 1.0 | 17.4 | 6.7 |
|  | 10 | 34.1 | 31.4 |
|  | 100 | NA | 72.6 |
| 9 | 0.1 | 1.8 | 6.7 |
|  | 1.0 | 27.9 | 0 |
|  | 10 | 32.8 | 0 |
|  | 100 | NA | 81.4 |
| 11 | 0.1 | 5.6 | 0 |
|  | 1.0 | 18.1 | 0 |
|  | 10 | 23.9 | 0 |
|  | 100 | 86.2 | 2.7 |
| 12 | 0.1 | 9.4 | 11.2 |
|  | 1.0 | 7.2 | 2.5 |
|  | 10 | 21.3 | 9.9 |
|  | 100 | 88.9 | 9.9 |
| 13 | 0.1 | 9.9 | 0 |
|  | 1.0 | 12.5 | 2.4 |
|  | 10 | 15.7 | 4.3 |
|  | 100 | 87.5 | 54.3 |
| 14 | 0.1 | 2.1 | 21.0 |
|  | 1.0 | 11.3 | 6.1 |
|  | 10 | 35.4 | 3.9 |
|  | 100 | 86.7 | 22.3 |
| Paromomycin | 2 mg/ml | 77.8 | 4.9 |

NA = not available due to cytotoxicity.

EXAMPLE 5

Testing Against the Microsporidian *Encephalitozoon* (*Septata*) *intestinalis*

Compounds 2, 10 and 15 were tested for i,7 vitro growth inhibitory activity against E. intestinalis, grown on African green monkey kidney cells (Vero cells). Vero cells were grown in 25-cm² culture flasks at 37° C. in a humidified 5% carbon dioxide incubator. Cultures were maintained in minimal essential medium (Gibco BRL, Gaithersburg, Md., U.S.A.), supplemented with L-glutamine, Earle's salts, 5% heat-inactivated foetal calf serum (Hyclone Labs, Inc., U.S.A.), fungizone (2 μg/ml, Gibco BRL) and gentamicin (50 μg/ml, Gibco BRL). E. intestinalis spores were collected from the supernatant of an infected Vero cell culture and were used to infect normal cells to produce a fresh spore preparation for growth inhibition tests.

Growth inhibition tests were performed in 24-well culture plates. One ml of Vero cells ($5 \times 10^4$ cells per ml) was placed in each well and the cells incubated for 12–15 hours at 37° C. The supernatant medium was then removed and replaced with 1 ml of medium containing $1.5-2.0 \times 10^4$ E. intestinalis spores per ml along with 1 μl of test compound dissolved in dimethylsulfoxide (DMSO) or DMSO alone for the control treatments without test compound. The plates were incubated at 37° C. and the medium was changed every 72 h along with fresh test compound in DMSO or DMSO alone (controls). After 2 weeks the supernatant was transferred from each well to a microcentiifuge tube, then concentrated by centrifugation with resuspension of the resulting E. intestinalis spore pellet in 300–500 μl fresh medium. The spore number in each sample was then determined by counting in a hemocytometer. The results in Table 11 show the effects of the test compounds on the number of spores and are expressed as a percentage of the spore number in the control treatment without test compound.

TABLE 11

Growth inhibitory activity of compounds against *E. intestinalis*

| Treatment | Concentration (μg/ml)* | Growth (% of control) |
| --- | --- | --- |
| Control |  | 100 |
| Compound 2 | 0.1 | 29 |
| Compound 10 | 1.0 | 20 |
| Compound 15 | 0.1 | 13 |

*test compounds showed no toxicity to Vero cells at these concentrations

What is claimed is:

1. A method for treating protozoal infections in an animal comprising applying to the locus of a protozoan a compound having the formula:

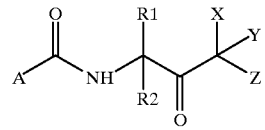

wherein;

A is selected from substituted and unsubstituted phenyl, pyridyl, furyl, thionyl, isoxazolyl, oxazolyl, pyrrolyl, isothiazolyl, thiazolyl, pyrazolyl, imidazolyl, pyrimidinyl, quinolyl, isoquinolyl, naphthyl, pyridazinyl, pyrazinyl, benzothienyl, indolyl, benzofuranyl, benzyl, $(C_3-C_7)$cycloalkyl, $(C_1-C_6)$ alkyl, halo$(C_1-C_6)$alkyl, $(C_2-C_6)$alkenyl, halo$(C_2-C_6)$ alkenyl, $(C_2-C_6)$alkynyl, and halo$(C_2-C_6)$alkynyl wherein the substituents are independently selected from:

a) one to four of halo, cyano, $(C_1-C_6)$alkyl, halo $(C_1-C_6)$alkyl, $(C_2-C_6)$alkenyl, halo$(C_2-C_6)$alkenyl, $(C_2-C_6)$alkynyl, halo$(C_2-C_6)$alkynyl, $(C_1-C_6)$ alkoxy, halo$(C_1-C_6)$alkoxy, $(C_1-C_6)$alkylthio, halo ($C_1$–$C_6$)alkylthio, nitro, —$NR^6R^7$, —$CR^8$=$NOR^9$, $NHCOOR^{10}$, —$CONR^{11}R^{12}$, $COOR^{13}$;
b) fused five, six, and seven membered rings formed from two such substituents; and
c) a fused 5, 6 or 7 membered carbocyclic ring which may contain up to two heteroatoms selected from the group consisting of: O, S, N, and P:

$R^1$ and $R^2$ are each independently selected from H, ($C_1$–$C_6$)alkyl, halo($C_1$–$C_6$)alkyl, ($C_2$–$C_6$)alkenyl, halo($C_2$–$C_6$)alkenyl, ($C_2$–$C_6$)alkynyl, or halo($C_2$–$C_6$)alkynyl provided that at least one of $R^1$ and $R^2$ is other than H;

$R^6$ and $R^7$ are each independently selected from H, ($C_1$–$C_6$)alkyl, and ($C_1$–$C_6$)alkylcarbonyl, $R^8$ is selected from H, ($C_1$–$C_6$)alkyl, ($C_2$–$C_6$)alkenyl, and ($C_2$–$C_6$)alkynyl;

$R^9$ is selected from H, ($C_1$–$C_6$)alkyl, ($C_2$–$C_6$)alkenyl, ($C_2$–$C_6$)alkynyl, and ($C_1$–$C_4$)alkylcarbonyl;

$R^{10}$, $R^{11}$, $R^{12}$ and $R^{13}$ are each independently selected from H, ($C_1$–$C_6$)alkyl, ($C_2$–$C_6$)alkenyl, and ($C_2$–$C_6$)alkynyl; and X, Y and Z are each independently selected from H, halo, cyano, thiocyano, isothiocyano and ($C_1$–$C_6$)alkylsulfonyloxy, provided that at least one of X, Y and Z is halo, cyano, thiocyano, isothiocyano or ($C_1$–$C_6$)alkylsulfonyloxy;

enantiomers and stereoisomers thereof; and physiologically acceptable acid addition salts thereof.

2. The method of claim 1 wherein the compound is of the formula:

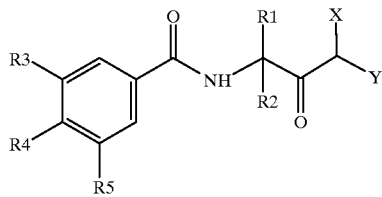

wherein:
$R^1$ and $R^2$ are each independently selected from H, ($C_1$–$C_6$)alkyl, halo($C_1$–$C_6$)alkyl, ($C_2$–$C_6$)alkenyl, and ($C_2$–$C_6$)alkynyl, provided that at least one of $R^1$ and $R^2$ is other than H;

$R^3$, $R^4$, and $R^5$ are each independently selected from the group consisting of H, halo, cyano, ($C_1$–$C_6$)alkyl, halo($C_1$–$C_6$)alkyl, ($C_2$–$C_6$)alkenyl, ($C_2$–$C_6$)alkynyl, ($C_1$–$C_6$)alkoxy, ($C_1$–$C_6$)alkylthio, halo($C_1$–$C_6$)alkoxy, nitro, —$NR^6R^7$, —$CR^8$=$NOR^9$, $NHCOOR^{10}$, —$CONR^{11}R^{12}$, —$COOR^{13}$, and a fused 5, 6 or 7 membered carbocyclic ring which may contain up to two heteroatoms selected from the group consisting of: O, S, N, and P;

$R^6$, $R^7$, $R^8$, $R^9$, $R^{10}$, $R^{11}$, $R^{12}$, and $R^{13}$ are each independently selected from H and ($C_1$–$C_6$) alkyl; and X and Y are each independently selected from H, halo, cyano, thiocyano, isithiocyano and ($C_1$–$C_6$) alkylsulfonyloxy, provided that at least one of X and Y is other than H.

3. The method of claim 2 wherein X is chloro; Y is H; $R^1$ is methyl; $R^2$ is selected from methyl and ethyl; $R^3$ and $R^5$ are each independently selected from H, halo, methyl, nitro, cyano, amino, —CH=$NOCH_3$ and —$NHCOOCH_3$; and $R_4$ is selected from H, halo, amino, cyano, —CH=$NOCH_3$, —$NHCOOCH_3$, $COOCH_3$, and ($C_1$–$C_4$) alkyl.

4. The method of claim 3 wherein X is chloro; Y is H; $R^1$ is methyl, $R^2$ is ethyl, $R^3$ and $R^5$ are each independently selected from halo, methyl, cyano, and —CH=$NOCH_3$; and $R^4$ is selected from H, amino, methyl, and —CH=$NOCH_3$.

5. The method of claim 1 wherein the compound is of the formula:

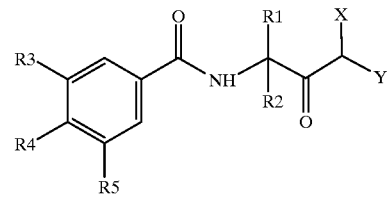

wherein:
$R^1$ and $R^2$ are independently selected from H, ($C_1$–$C_6$) alkyl, halo($C_1$–$C_6$)alkyl, ($C_2$–$C_6$)alkenyl, and ($C_2$–$C_6$) alkynyl, provided that at least one of $R^1$ and $R^2$ is other than H;

$R^3$ and $R^4$, are each independently selected from H, halo, cyano, ($C_1$–$C_6$)alkyl, halo($C_1$–$C_6$)alkyl, ($C_2$–$C_6$)alkenyl, ($C_2$–$C_6$)alkynyl, ($C_1$–$C_6$)alkoxy, ($C_1$–$C_6$)alkylthio, halo($C_1$–$C_6$)alkoxy, nitro, —$NR^6R^7$, —$CR^8$=$NOR^9$, $NHCOOR^{10}$, —$CONR^{11}R^{12}$, and —$COOR^{13}$;

$R^6$, $R^7$, $R^8$, $R^9$, $R^{10}$, $R^{11}$, $R^{12}$, and $R^{13}$ are H or ($C_1$–$C_6$) alkyl; and X and Y are each independently selected from H, halo, cyano, thiocyano, isothiocyano and ($C_1$–$C_6$) alkysulfonyloxy, provided that at least one of X and Y is other than H.

6. The method of claim 1 wherein the compound is applied at a dose of from 1.0 mg to 200.0 mg per kilogram bodyweight per day.

7. The method of claim 1 wherein the protozoan is selected from one or more of Giardia species, Leishmania species, Toxoplasma species, Cryptosporidium species, Entamoeba species, and microsporidia species.

* * * * *